(12) United States Patent
Sato et al.

(10) Patent No.: US 8,003,409 B2
(45) Date of Patent: Aug. 23, 2011

(54) SEMICONDUCTOR NANOPARTICLE FLUORESCENT REAGENT AND FLUORESCENCE DETERMINATION METHOD

(75) Inventors: Keiichi Sato, Tokyo (JP); Susumu Kuwabata, Osaka (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 1534 days.

(21) Appl. No.: 11/389,151

(22) Filed: Mar. 27, 2006

(65) Prior Publication Data

US 2006/0174821 A1    Aug. 10, 2006

Related U.S. Application Data

(62) Division of application No. 10/360,866, filed on Feb. 10, 2003, now abandoned.

(30) Foreign Application Priority Data

Mar. 27, 2002   (JP) .................................. 2002/88987

(51) Int. Cl.
*G01N 33/553* (2006.01)
*B32B 5/16* (2006.01)
(52) U.S. Cl. ........ 436/525; 436/546; 436/164; 436/172; 424/9.42; 424/9.6; 427/213.3; 427/214; 427/215; 428/402.24; 428/404
(58) Field of Classification Search ............... 436/525, 436/546, 164, 172; 428/402.24, 404; 424/9.42, 424/9.6; 427/213.3, 214, 215
See application file for complete search history.

(56) References Cited

U.S. PATENT DOCUMENTS

| 5,906,670 | A | 5/1999 | Dobson et al. |
| 6,194,213 | B1 | 2/2001 | Barbera-Guillem |
| 6,306,610 | B1 | 10/2001 | Bawendi et al. |
| 6,319,426 | B1 | 11/2001 | Bawendi et al. |
| 6,333,110 | B1 * | 12/2001 | Barbera-Guillem ..... 428/402.24 |
| 6,649,138 | B2 | 11/2003 | Adams et al. |
| 6,984,491 | B2 * | 1/2006 | Mirkin et al. ..................... 435/6 |
| 2001/0055764 | A1 * | 12/2001 | Empedocles et al. ............ 435/6 |
| 2004/0007169 | A1 | 1/2004 | Ohtsu et al. |
| 2004/0031519 | A1 | 2/2004 | Andriessen |

FOREIGN PATENT DOCUMENTS

| WO | WO 01/42489 A1 | 12/2000 |
| WO | WO 01/61045 A1 | 2/2001 |

OTHER PUBLICATIONS

Hasselbarth et al. Chemical Physics Letters. vol. 203. No. 2, 3. Feb. 19, 1993; p. 271-276.*
Matsumoto et al. American Chemical Society 1996, p. 13781-13785.*
Torimoto et al. Fabrication of CdS nanoparticle chains along DNA double strands. The Journal of Physical Chemistry B, vol. 103, No. 42, Oct. 21, 1999.*

(Continued)

*Primary Examiner* — Jacob Cheu
*Assistant Examiner* — Pensee Do
(74) *Attorney, Agent, or Firm* — Stites & Harbison PLLC; Juan Carlos A. Marquez, Esq.

(57) ABSTRACT

The present invention measures defect fluorescence exhibited from a defect level mainly on a semiconductor nanoparticle surface site which has an energy level existing inside the forbidden band of energy levels inside the semiconductor nanoparticle.

14 Claims, 7 Drawing Sheets

OTHER PUBLICATIONS

Yongchi Tian et al., "Coupled Composite CdS-CdSe and Core-Shell Types of (CdS)CdSe and (CdSe)CdS Nanoparticles", J. Phys. Chem. 1996, vol. 100, No. 21, 1996 American Chemical Society, pp. 8927-8939.

Hyeong-Chan Youn et al., "Dihexadecyl Phosphate, Vesicle-Stabilized and in Situ Generated Mixed CdS and ZnS Semiconductor Particles, Preparation and Utilization for Photosensitized Charge Separation and Hydrogen Generation", J. Phys. Chem. 1988, vol. 92, No. 22, 1988 American Chemical Society, pp. 6320-6327.

A. R. Kortan et al., "Nucleation and Growth of CdSe on ZnS Quantum Crystallite Seeds, and Vice Versa, in Inverse Micelle Media", J. Phys. Chem. 1990, vol. 112, No. 4, 1990 American Chemical Society, pp. 1327-1332.

B. O. Dabbousi et al., (CdSe) ZnS Core-Shell Quantum Dots: Synthesis and Characterization of a Size Series of Highly Luminescent Nanocrystallites, J. Phys. Chem. 1997, vol. 101, No. 46, 1997 American Chemical Society, pp. 9463-9475.

Lubomir Spanhel et al., "Photochemistry of Colloidal Semiconductors, 20. Surface Modification and Stability of Strong Luminescing CdS Particles" J. Phys. Chem. 1987, vol. 109, No. 19, 1987 American Chemical Society, pp. 5649-5655.

A.P. Alivisatos, "Perspectives on the Physical Chemistry of Semiconductor Nanocrystals", J. Phys. Chem. 1996, vol. 100, No. 31, 1996 American Chemical Society, pp. 13226-13239.

Hedi Mattoussi et al., "Self-Assembly of CdSe-ZnS Quantum Dot Bioconjugates Using an Engineered Recombinant Protein", J. American Phys. Chem. 2000, vol. 122, No. 49, 2000, pp. 12142-12150.

Kerry P. McNamara and Zeev Rosenzweig, "Dye-Encapsulating Liposomes as Fluorescence-Based Oxygen Nanosensors", Anal. Chem., vol. 70, No. 22, Nov. 15, 1998, p. 4853-4859.

Dubertret et al., "In Vivo Imaging of Quantum Dots Encapsulated in Phospholipid Micelles", Science, vol. 298, Nov. 29, 2002, pp. 1759-1762.

European Search Report dated Oct. 13, 2003.

* cited by examiner

SEMICONDUCTOR NANOPARTICLE FLUORESCENT REAGENT AND FLUORESCENCE DETERMINATION METHOD

CROSS REFERENCE TO RELATED APPLICATIONS

This application is a Divisional application of nonprovisional U.S. Ser. No. 10/360,866 filed on Feb. 10, 2003 now abandoned. Priority is claimed based upon U.S. application Ser. No. 10/360,866 filed on Feb. 10, 2003, which claims the priority date of Japanese Patent Application 2002-088987 filed on Mar. 27, 2002.

BACKGROUND OF THE INVENTION

1. Technical Field

The present invention relates to a fluorescent reagent using semiconductor nanoparticles, and a fluorescence determination method using semiconductor nanoparticles.

2. Background Art

Semiconductor nanoparticles of a grain size of 10 nm or less are located in the transition region between bulk semiconductor crystals and molecules. Their physicochemical properties are therefore different from both bulk semiconductor crystals and molecules. In this region, the energy gap of a semiconductor nanoparticle increases as its grain size decreases, due to the occurrence of a quantum-size effect. In addition, the degeneracy of the energy band that is observed in bulk semiconductors is removed and the orbits are dispersed. As a result, a lower-end of the conduction band is shifted to the negative side and an upper-end of the valence band is shifted to the positive side.

Semiconductor nanoparticles can be easily prepared by dissolving equimolar amounts of precursors of Cd and X (X being S, Se or Te). This is also true for their manufacture using CdSe, ZnS, ZnSe, HgS, HgSe, PbS, or PbSe, for example.

The reason semiconductor nanoparticles are attracting attention is that since semiconductor nanoparticles are characterized by emitting strong fluorescence with a narrow full width at half maximum, the creation of various colors of fluorescence is possible. Thus, it is considered that future applicable fields are almost unlimited. However, semiconductor nanoparticles obtained by the above method exhibit a wide grain-size distribution and therefore cannot provide the full advantage of the properties of semiconductor nanoparticles.

Therefore, attempts have been made to attain a monodisperse distribution by using chemical techniques to precisely separate the semiconductor nanoparticles having a wide grain-size distribution immediately after preparation into individual grain sizes and extract only those semiconductor nanoparticles of a particular grain size. The attempts to attain a monodisperse distribution of grain size that have been reported so far include an electrophoresis separation method that utilizes variation in the surface charge of nanoparticles depending on the grain size, an exclusion chromatography that takes advantage of differences in retention time due to different grain sizes, a size-selective precipitation method utilizing differences in dispersibility into an organic solvent due to different grain sizes, and a size-selective optical etching method that takes advantage of the fact that a metal chalcogenide semiconductor is oxidatively dissolved when irradiated by light in the presence of dissolved oxygen.

Semiconductor nanoparticles obtained by these methods exhibit a spectrum having a peak with a relatively narrow full width at half maximum (FWHM). Thus, by controlling the grain size of semiconductor nanoparticles, various reagents exhibiting a spectrum having narrow FWHMs can be prepared. This enables multicolor analyses for the detection and imaging of biopolymers. Further, semiconductor nanoparticles have greater durability compared with commonly used organic dyes, and they are almost free from fading.

Also, in addition to band gap fluorescence exhibited by the inner part of semiconductor nanoparticles, semiconductor nanoparticles emit defect fluorescence that is completely different from fluorescence arising from an energy level existing in the forbidden band of energy levels inside semiconductor nanoparticles.

The energy level that emits the defect fluorescence is presumably derived from the presence of a defect level mainly on the surface site of semiconductor nanoparticles and is considered to inhibit the properties of semiconductor nanoparticles exhibiting a spectrum with a narrow FWHM, and thus this has been a problem to be solved. Further, as described later using FIG. 2, when semiconductor nanoparticles are prepared using a size-selective optical etching method or the like, the phenomena may be observed where defect fluorescence generated from the defect level is more strongly emitted than inherent fluorescence generated from the band gap inside the semiconductor nanoparticles. In the present invention, fluorescence that is exhibited due to the presence of a defect level mainly on the surface site of semiconductor nanoparticles is called "defect fluorescence."

As a typical solution method to overcome the effect of this defect fluorescence, a method has been attempted which carries out multi-layering on the semiconductor material for the particle by coating the core with a semiconductor material having a broader band gap than the semiconductor material for the core, and inorganic and organic materials, and suppresses the defect fluorescence. Experiments by this method have been carried out with various materials. However, because the preparation of semiconductor nanoparticles by this method requires the safety of reagents and a reaction at relatively higher temperatures, the method can be hardly said to be industrially preferable. When semiconductor nanoparticles are not multi-layered, the phenomena may be observed where florescence generated from the defect level thereof is stronger than inherent fluorescence generated from the band gap inside semiconductor nanoparticles.

Therefore, there has been a need to solve the problem of defect fluorescence inhibiting measurement of the inherent fluorescence of semiconductor nanoparticles.

SUMMARY OF THE INVENTION

The present inventors have made intensive studies and succeeded in solving the above problem by, conversely, making positive use of defect fluorescence, which heretofore had been considered as something that obstructs various measurements utilizing the inherent fluorescence emission of semiconductor nanoparticles. Namely, in addition to fluorescence having an energy level existing in the forbidden band of energy levels inside semiconductor nanoparticles, the use of defect fluorescence exhibited due to the presence of a defect level mainly on the surface site of semiconductor nanoparticles has provided the solution to the above problem.

Firstly, a fluorescent reagent of the present invention is characterized by measuring defect fluorescence exhibited due to the presence of a defect level mainly on the surface site of semiconductor nanoparticles.

The fluorescent reagent of the present invention is preferably used, for example, for the detection of biopolymers.

The detection of biopolymers can use DNA chips or beads using hybridization. In particular, DNA chips or beads can be used when the biopolymers are DNAs or proteins.

Further, the fluorescent reagent of the present invention is preferably used for vital observation. In particular, it can be used as a stain for living tissues in cell technologies.

Furthermore, by modifying the surface of the semiconductor nanoparticles, the fluorescent reagent of the present invention can be chemically bound to the biopolymers or living tissues via the modifying groups. Alternatively, by giving an electric charge to the semiconductor nanoparticles by surface modification, the fluorescent reagent can be electrostatically bound to the biopolymers or living tissues. The surface of the semiconductor nanoparticles can be modified with functional groups.

Moreover, defect fluorescence of the semiconductor nanoparticles can be amplified using a size-selective optical etching method.

Secondly, a method of measuring fluorescence of the present invention comprises the step of measuring defect fluorescence exhibited due to the presence of a defect level mainly on the surface site of a semiconductor nanoparticle.

As a specific example of the measurement method, the method is preferably applied to a biopolymer detection method that detects the presence or absence of and the amount of binding to probe biopolymers by electrostatically binding positively or negatively charged semiconductor nanoparticles to a negative or positive charge of sample biopolymers. The biopolymer detection method measures defect fluorescence exhibited due to the presence of a defect level mainly on the surface site of a semiconductor nanoparticle.

Here, the biopolymer detection can utilize DNA chips or beads using hybridization. The biopolymers are preferably DNAs or proteins.

Other specific examples of the measurement method include application to vital observation. For example, the vital observation that utilizes semiconductor nanoparticles as stains for living tissues in cell technologies may be mentioned. Other examples include the use of semiconductor nanoparticles as stains for living tissue such as viscera, muscle, brain, and bone.

Further, the measurement method of the present invention is applicable to the biopolymer detection wherein the surfaces of the semiconductor nanoparticles are modified with functional groups, as previously filed by the present applicant in Japanese Patent Application No. 2002-27616.

When the semiconductor nanoparticles are manufactured by a size-selective optical etching method, the defect fluorescence thereof is amplified.

Furthermore, the defect fluorescence can be remarkably exhibited when excited with excitation light of a wavelength deviated from an excitation wavelength at which fluorescence emission from a band gap of the semiconductor nanoparticles exhibits a peak.

Moreover, in the fluorescence measurement method of the present invention, two or more types of defect fluorescence having different wavelengths can be measured by using two or more types of semiconductor nanoparticles, thus enabling multicolor analysis to obtain two or more types of information.

Further, defect fluorescence having different spectra of a semiconductor nanoparticle can be measured by changing excitation wavelengths, and a difference between the different spectra can be obtained to enable correction of a measurement error.

As described above, the present invention relates to a fluorescent reagent which utilizes defect fluorescence arising from a defect level of a surface site existing inside the forbidden band of a band gap of a semiconductor nanoparticle material, and a method of measuring fluorescence.

There are two types of fluorescence emitted from a semiconductor nanoparticle. One is band gap fluorescence attributable to the properties of a semiconductor nanoparticle material per se, and the other is defect fluorescence mainly attributable to the properties of a surface site of a prepared semiconductor nanoparticle. Band gap fluorescence attributable to the properties of the semiconductor nanoparticle per se can be controlled by controlling the grain size of semiconductor nanoparticles, and the control range is determined depending on the material of the semiconductor nanoparticles. The band gap fluorescence exhibits a spectrum having a peak with a very narrow FWHM. In contrast, the defect fluorescence of semiconductor nanoparticles is not related to the grain size of semiconductor nanoparticles, and is determined depending only on the materials constituting the semiconductor nanoparticle. The spectrum of the defect fluorescence has a wider FWHM compared with that of the band gap fluorescence, but the fluorescence intensity of the defect fluorescence is equal to or stronger than that of band gap fluorescence from mono-layered semiconductor nanoparticles. Therefore, when observing fluorescence of several colors, the defect fluorescence allows semiconductor nanoparticles to fully exhibit their abilities as a reagent.

This fluorescence is strongly exhibited in the case of ZnS when zinc perchlorate and hydrogen sulfide gas are mixed in a nitrogen atmosphere. Further, in the case of CdS, after cadmium perchlorate and hydrogen sulfide gas are mixed in a nitrogen atmosphere and the grain size is monodispersed by an optical etching method, the fluorescence is strongly exhibited. Furthermore, semiconductor nanoparticles prepared by methods other than the above exhibit defect fluorescence in most cases.

In addition to the above semiconductor nanoparticle materials, examples of the materials to be used in the present invention include ZnO, ZnS, ZnSe, ZnTe, CdO, CdS, CdSe, CdTe, HgS, HgSe, HgTe, InP, InAs, GaN, GAP, GaAs, TiO, $WO_3$, PbS, and PbSe.

EXAMPLES

Figure 1:
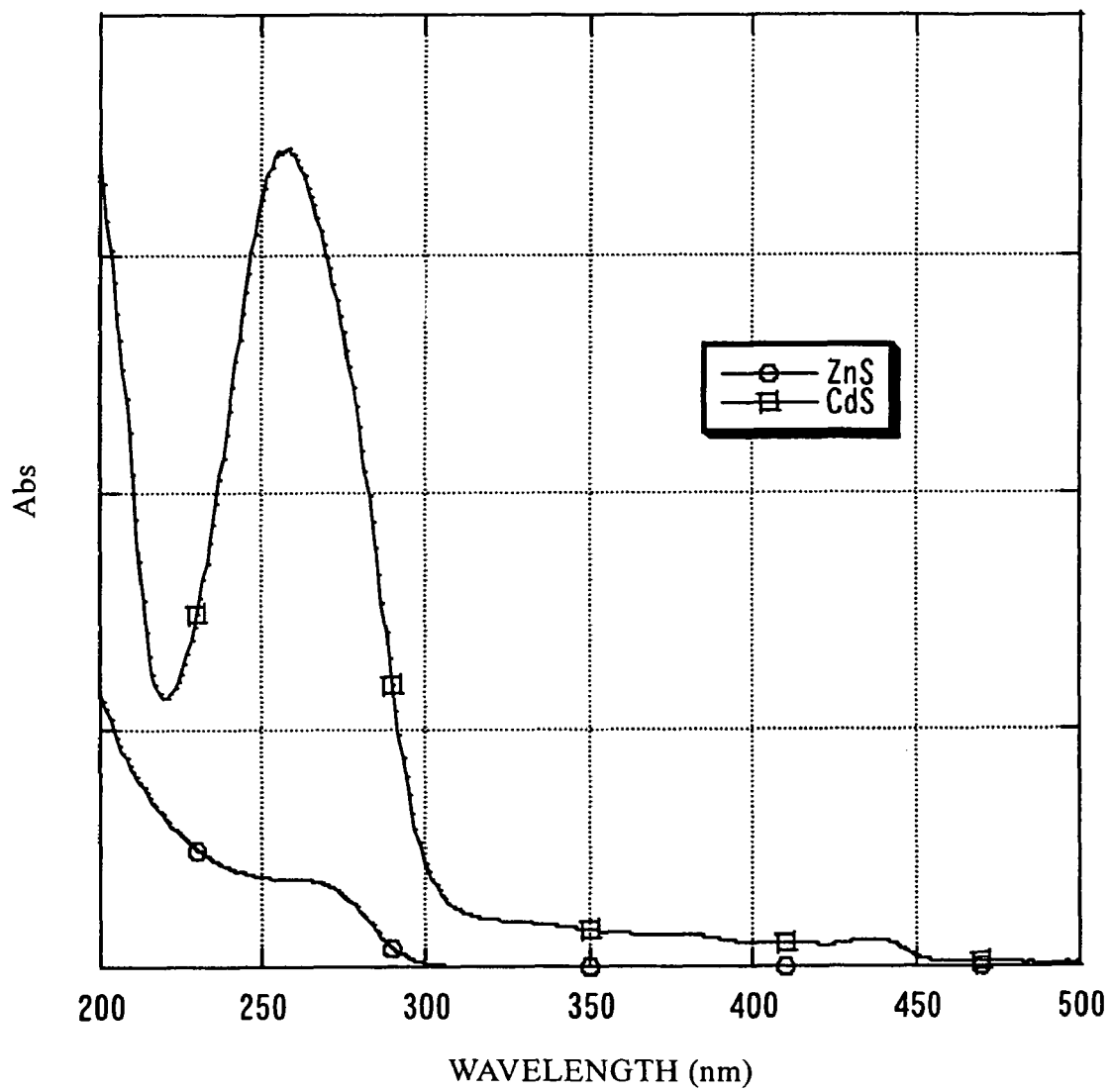
FIG. 1 shows the absorption spectra of semiconductor nanoparticles.

Herein, CdS nanoparticles and ZnS nanoparticles are referred to for description of the method for preparing semiconductor nanoparticles according to the present invention.

Preparation of CdS Semiconductor Nanoparticles

In a semiconductor particle, the proportion of its surface area to its volume is very large, and thus semiconductor nanoparticles tend to coalesce very easily. Therefore, in order to allow the semiconductor nanoparticles to exist stably, measures have to be taken to prevent them from colliding or fusing with each other. A variety of measures have been devised so far, which can be roughly divided into two types. One is the physical isolation of the semiconductor nanoparticles by incorporating them into a solid matrix and a polymer matrix. The other is the inactivation of the particle surface by chemically modifying a metal-ion site on the particle surface with a low-molecule organic matter having a high capacity for forming a complex with the metal-ion site. Based on the latter concept, hexametaphosphate was employed as the stabilizer for the present example.

1000 ml of an aqueous solution of sodium hexametaphosphate (0.1 mmol) and cadmium perchlorate (0.2 mmol) was prepared and adjusted to pH 10.3. Nitrogen gas was bubbled into the solution, and then hydrogen sulfide gas (0.2 mmol) was injected into the solution while stirring vigorously. Thereafter, stirring was conducted for a while, during which time the solution changed from optically transparent and colorless to optically transparent yellow.

At this point, semiconductor nanoparticles that were stabilized by hexametaphosphate already existed in the solution, but these semiconductor nanoparticles had a wide grain-size distribution, with their standard deviation being 15% or more of the average grain size. In addition, the semiconductor nanoparticles in this state had very weak band gap fluorescence intensity and defect fluorescence intensity.

Hereafter, the size-selective photocorrosion is described. As the physicochemical properties of a semiconductor nanoparticle depend on its grain size due to a quantum-size effect, the physical properties of the semiconductor nanoparticles in this state are averaged and their characteristics cannot be fully exhibited. Thus, there is a need to chemically separate the semiconductor nanoparticles having a wide grain-size distribution immediately after preparation into individual grain sizes in an accurate manner, and extract only those semiconductor particles of a specific grain size in order to attain a monodisperse distribution. One of methods for carrying out the above operation is the size-selective photocorrosion. The size-selective photocorrosion takes advantage of the fact that as the grain size of a semiconductor nanoparticle decreases its energy gap increases due to a quantum-size effect, and the fact that a metal chalcogenide semiconductor is oxidatively dissolved when irradiated by light in the presence of dissolved oxygen. Thus, the method irradiates the semiconductor nanoparticles having a wide grain-size distribution with monochromatic light of a shorter wavelength than the wavelength of the semiconductor nanoparticle's absorption edge. This causes only the semiconductor nanoparticles of larger diameters to be selectively optically excited and dissolved, thus sorting the semiconductor nanoparticles into smaller grain sizes. In this process, semiconductor nanoparticles in the solution become monodispersed and come to have a band gap fluorescence exhibiting a spectrum with a narrow FWHM in accordance with the irradiated monochromatic light and the grain size of the semiconductor nanoparticle. In contrast, defect fluorescence, which seems to be attributable to the energy level mainly on the semiconductor nanoparticle surface, is of relatively stronger intensity than the band gap fluorescence. Normally such defect fluorescence is regarded as a factor inhibiting the properties of a semiconductor nanoparticle, and is thus treated as a problem, but in the present invention this defect fluorescence is utilized. In the present invention, a size-selective optical etching reaction is used for the purpose of amplifying defect fluorescence.

Nitrogen gas was bubbled into a solution of semiconductor nanoparticles stabilized by hexametaphosphate and having a wide grain-size distribution, and then bubbling with oxygen was carried out for 10 minutes. Methyl viologen was added to the solution to a concentration of 50 µmol/l, and the solution was irradiated with a laser beam under stirring. In the present invention, the monochromatic light irradiation was carried out to optically dissolve semiconductor nanoparticles, and the wavelength of the monochromatic light was 450 nm.

When irradiated with a light of a wavelength of 476.5 nm, the resultant semiconductor nanoparticles had an average grain size of 3.2 nm and a standard deviation of 0.19 nm, thus exhibiting a very narrow grain-size distribution where the standard deviation was about 6% of the average grain size. Thus, a solution of semiconductor nanoparticles with an almost close-to-monodisperse distribution was obtained (FIG. 1). Further, the obtained semiconductor nanoparticles exhibited extremely high defect fluorescence (FIGS. 2 and 3).

Figure 2:
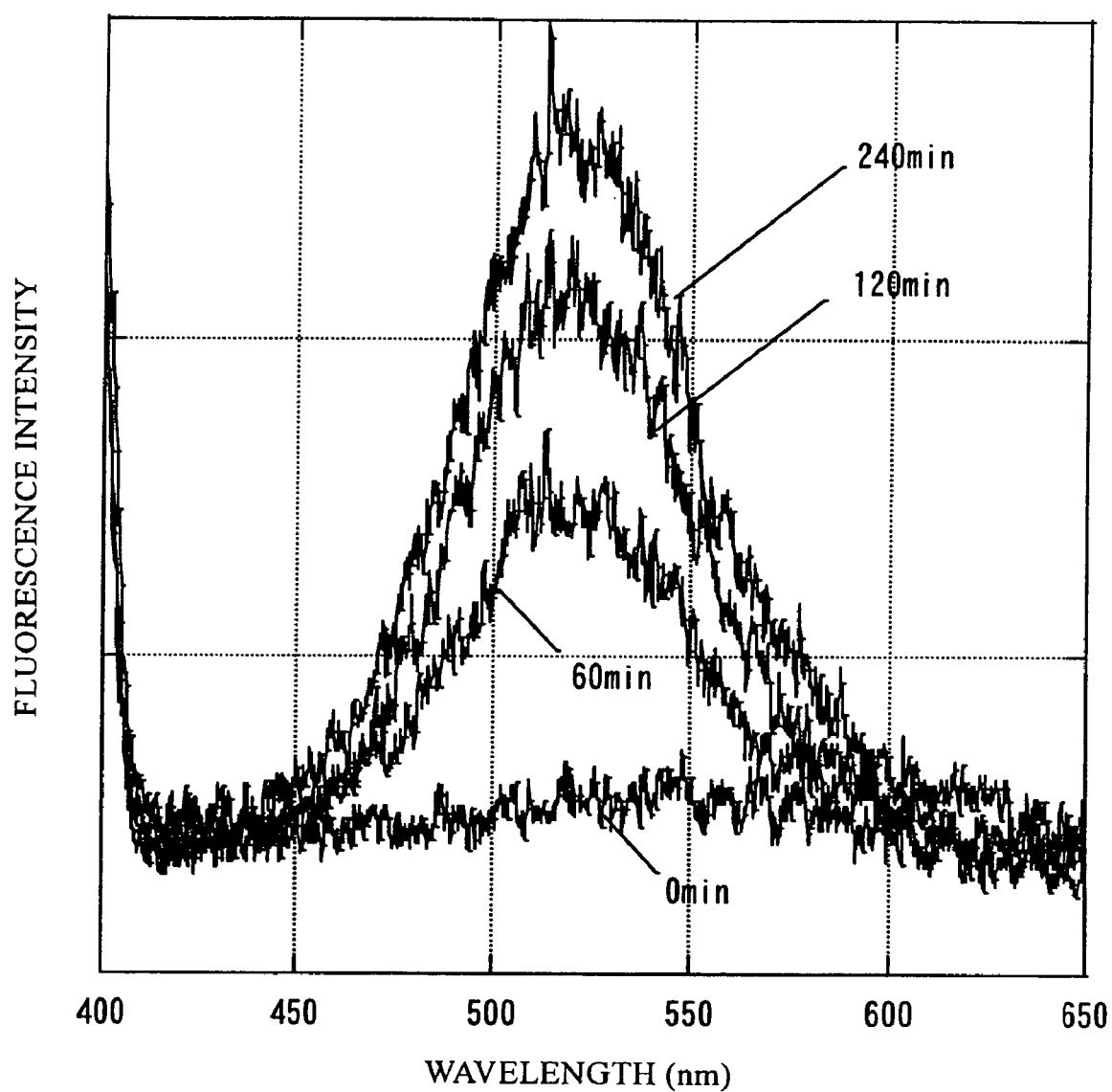
FIG. 2 shows the correlation between single color irradiation time and fluorescent spectrum of CdS nanoparticles.
Figure 3:
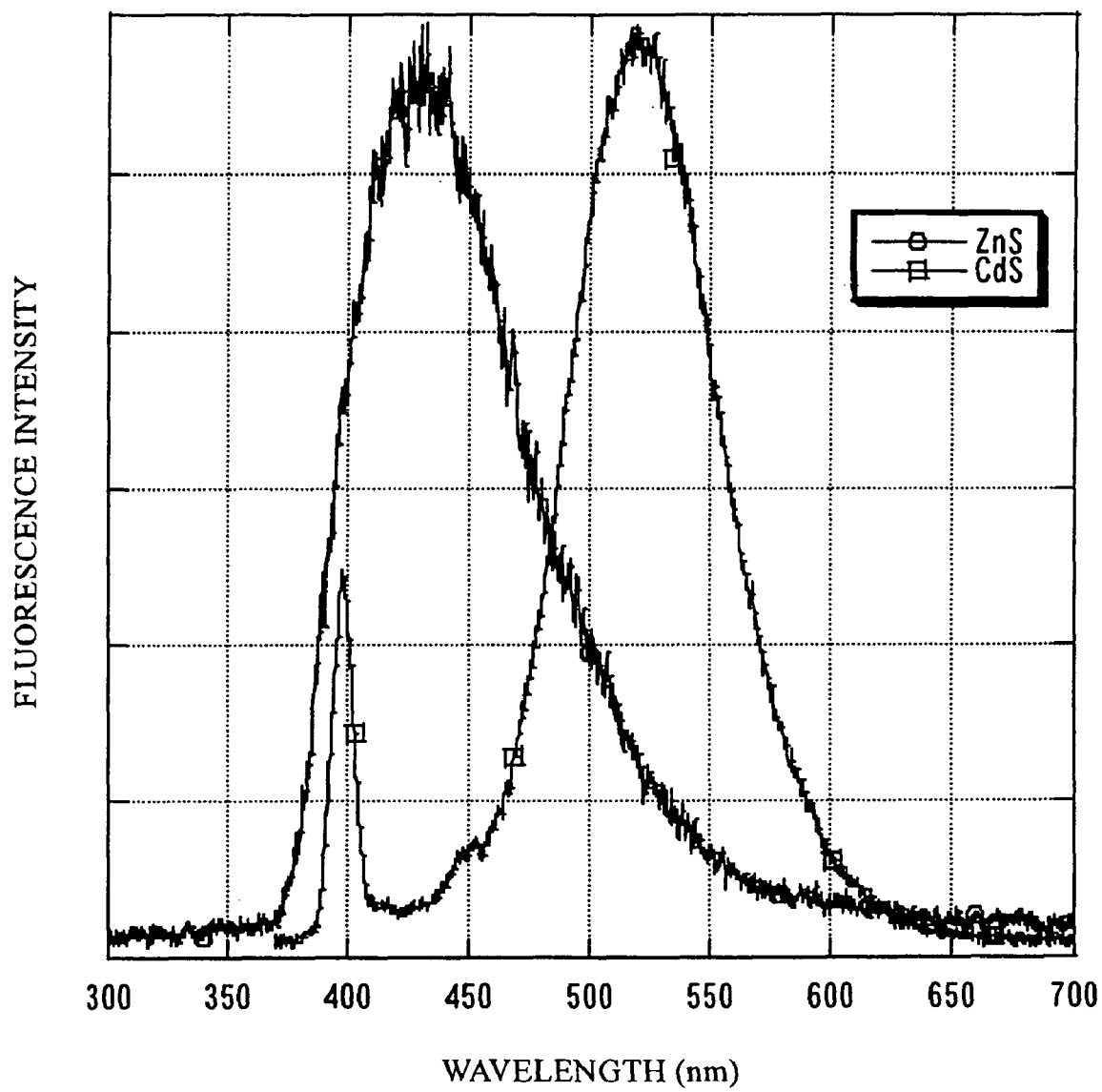
FIG. 3 shows the fluorescence spectra of semiconductor nanoparticles.

As shown in FIG. 2, it was found that with the progress of the size-selective photocorrosion process, the defect fluorescence increased its intensity.

Preparation of ZnS Semiconductor Nanoparticles

This method employed the same stabilizer, hexametaphosphate, as the method for CdS nanoparticles. 1000 ml of an aqueous solution of sodium hexametaphosphate (0.1 mmol) and cadmium perchlorate hexahydrate(0.2 mmol) was prepared and adjusted to pH 10.3. Nitrogen gas was bubbled into the solution, and hydrogen sulfide gas (0.2 mmol) was injected into the solution while stirring vigorously. Stirring was continued for a while thereafter, during which time the solution was optically transparent and colorless. As shown in FIG. 3, while CdS semiconductor nanoparticles did not have a strong intensity of defect fluorescence at this stage, ZnS semiconductor nanoparticles already had adequate defect fluorescence intensity. As shown in FIG. 3, the use of multi-wavelengths was also available by using defect fluorescence of two or more types of semiconductor nanoparticles at the same time. Thus, multicolor analysis could be conducted to obtain two or more types of information at the same time.

Although semiconductor nanoparticles herein were prepared by dissolving and stirring equimolar amounts of precursors of Cd or Zn, and precursors of S, the method for their preparation is not limited thereto.

Further, with respect to materials of semiconductor nanoparticles, the methods concerning CdS and ZnS were exemplified, but there are many materials which have band gaps to the above CdS and ZnS but exhibit fluorescence having the same properties as that of CdS and ZnS. Thus, the materials are not limited thereto. Furthermore, the defect fluorescence can be remarkably exhibited even though the grain-size of semiconductor nanoparticles is not monodispersed.

Next, application examples using defect fluorescence of semiconductor nanoparticles will be described.

Application Example of Positively Charged Semiconductor Nanoparticles

Semiconductor nanoparticles obtained by the above methods and the like, have substantial defect fluorescence, and in the case of a single obtained semiconductor nanoparticle, as a matter of course, the filed of application thereof can be further expanded by modifying the semiconductor nanoparticle surface with a functional group to produce a semiconductor nanoparticle having a functional group exposed on its surface.

The mechanism for detection of biopolymers will be described with reference to FIG. 4. In the figure, by binding between a positive charge of a surface substrate 1 forming a planar shape or bead shape and a negative charge of a phosphate side-chain of a probe DNA 2, the probe DNA 2 was immobilized to the substrate 1. The probe DNA 2 and a sample DNA 3 then hybridized to each other through hydrogen bonding. As a result, a negative charge of a phosphate side-chain of the sample DNA 3 increased. A positively charged semiconductor nanoparticle 4 bound to the negative charge of the sample DNA 3, and based on the amount of bound semiconductor nanoparticles, information concerning the hybridized sample DNA 3 was provided as a signal.

Figure 4:
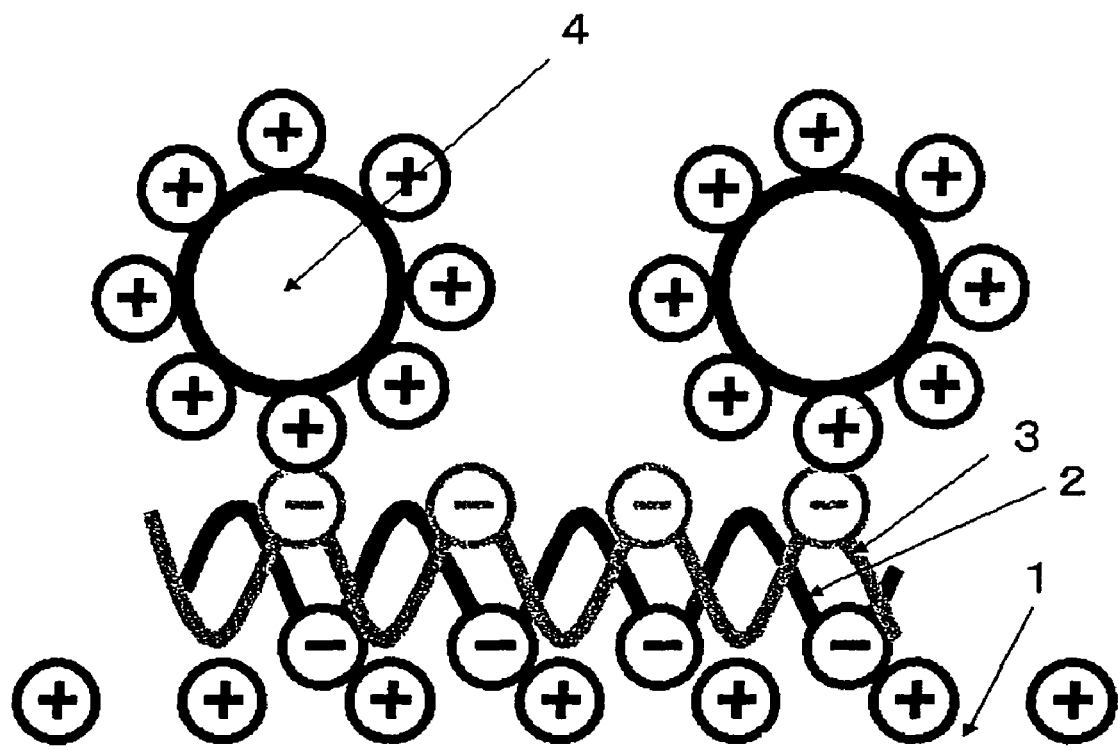
FIG. 4 is a schematic view of positively charged semiconductor nanoparticles.

In the example of FIG. 4, the probe DNA 2 and the semiconductor nanoparticle 4 were negatively and positively charged, respectively, but the charges may be the reverse thereof. Proteins and the like have isoelectric points, and thus the charge of the sample DNA 3 varies between positive and negative depending on the fluctuation of pH values. When the sample DNA 3 is positively charged, a negatively charged semiconductor nanoparticle 4 may be used.

Hereinafter, an application example wherein a reaction surface is modified with thiocholine ((2-mercaptoethyl)trimethylammonium) is described.

350 mg of acetyl thiocholine iodide was dissolved into 1.2 $cm^3$ of nitrogen-saturated 2 $mol \cdot dm^{-3}$ HCl aqueous solution, and the mixture was allowed to stand for 12 hours at room temperature. 0.2 $cm^3$ of 28% ammonia water in a nitrogen atmosphere was added to the mixture for neutralization, to thus prepare alkalescent 0.86 $mol \cdot dm^{-3}$ thiocholine ((2-mercaptoethyl)trimethylammonium) aqueous solution. By modifying the surface of nanoparticles with this solution, thiocholine-modified CdS nanoparticles having a positive charge on the particle surface were prepared. 4.65 ml of the solution was added to a CdS nanoparticle solution after size-selective optical etching, and the resultant solution was left under stirring for 24 hours at room temperature.

The semiconductor nanoparticles obtained above were positively charged and easily adsorbed onto negatively charged DNAs or proteins or the like. Here, an example of application to a DNA microarray using this property will be described. The DNA microarray method is a method wherein: a large number of known probe DNAs are chemically immobilized on a substrate; sample DNAs to be assayed are then introduced on top of the probes; and the sequence characteristics of the samples are identified based on the presence or absence of, and the amount of, binding between the probe DNAs and sample DNAs. Until now, the following method has been generally used to determine the existence of DNA binding and the amount of binding. That is, samples are modified with fluorescent substances or radioactive substances, and the existence of binding and the amount thereof is then determined by optically detecting these substances. The present invention does not require pre-treatment for modifying samples, and thus has a feature of requiring no sample pre-treatment by RNA reverse transcription or PCR reaction.

A sample DNA solution was dropped on a DNA microarray, and a cover glass was gently placed on the mixture. Then, the mixture was reacted for 16 hours under a hermetically closed environment using CHBIO (Hitachi Software Engineering Co., Ltd.). After the reaction, a slide glass was taken out therefrom, and the slide glass was soaked in a 2×SSC, 0.1% SDS solution and the cover glass was removed. Then, the slide glass was soaked for 2 hours in a 2×SSC, 0.1% SDS solution having a CdS semiconductor nanoparticle concentration of $1.2 \times 10^{17}$ $mol \cdot dm^{-3}$.

Thereafter, the slide glass was shaken in a 2×SSC, 0.1% SDS solution for 20 minutes at room temperature and shaken in a 0.2×SSC, 0.1% SDS solution for 20 minutes at room temperature. Further, in order to remove non-specific adsorptive samples, the slide glass was shaken in 0.2×SSC, 0.1% SDS solution for 20 minutes at 55° C., and the same operation was repeated. Then, the slide glass was shaken several times in 0.2×SSC, 0.1% SDS solution at room temperature, and shaken several times at room temperature in solutions of 0.2×SSC and 0.05×SSC, respectively. The above soaking and washing processes were carried out using a staining jar. The slide glass was then centrifuged and dried, and provided for analysis which was performed by filtering only defect fluorescence of semiconductor nanoparticles with an epi-illumination fluorescence microscope. As a result, bright red defect fluorescence was measured from each spot of the DNA microarray. According to the present example, it was found that the measurement of defect fluorescence of semiconductor nanoparticles was useful for reaction measurement in various reactions using semiconductor nanoparticles.

The present method is applicable to biopolymer microarrays in general, and not only to DNA microarrays but also other biopolymer microarrays and sensors such as protein microarrays, which have the same principle.

Multicolor Analysis Using Defect Fluorescence

As described above, defect fluorescence of semiconductor nanoparticles is determined only depending on the materials constituting the semiconductor nanoparticles, and irrespective of the grain-size of semiconductor nanoparticles. Therefore, in order to achieve multicolor analysis and observation using defect fluorescence, it is necessary to use semiconductor nanoparticles formed of the same number of materials as the number of colors to be used. Herein, multicolor analysis using CdS and ZnS nanoparticles will be described.

Figure 5:
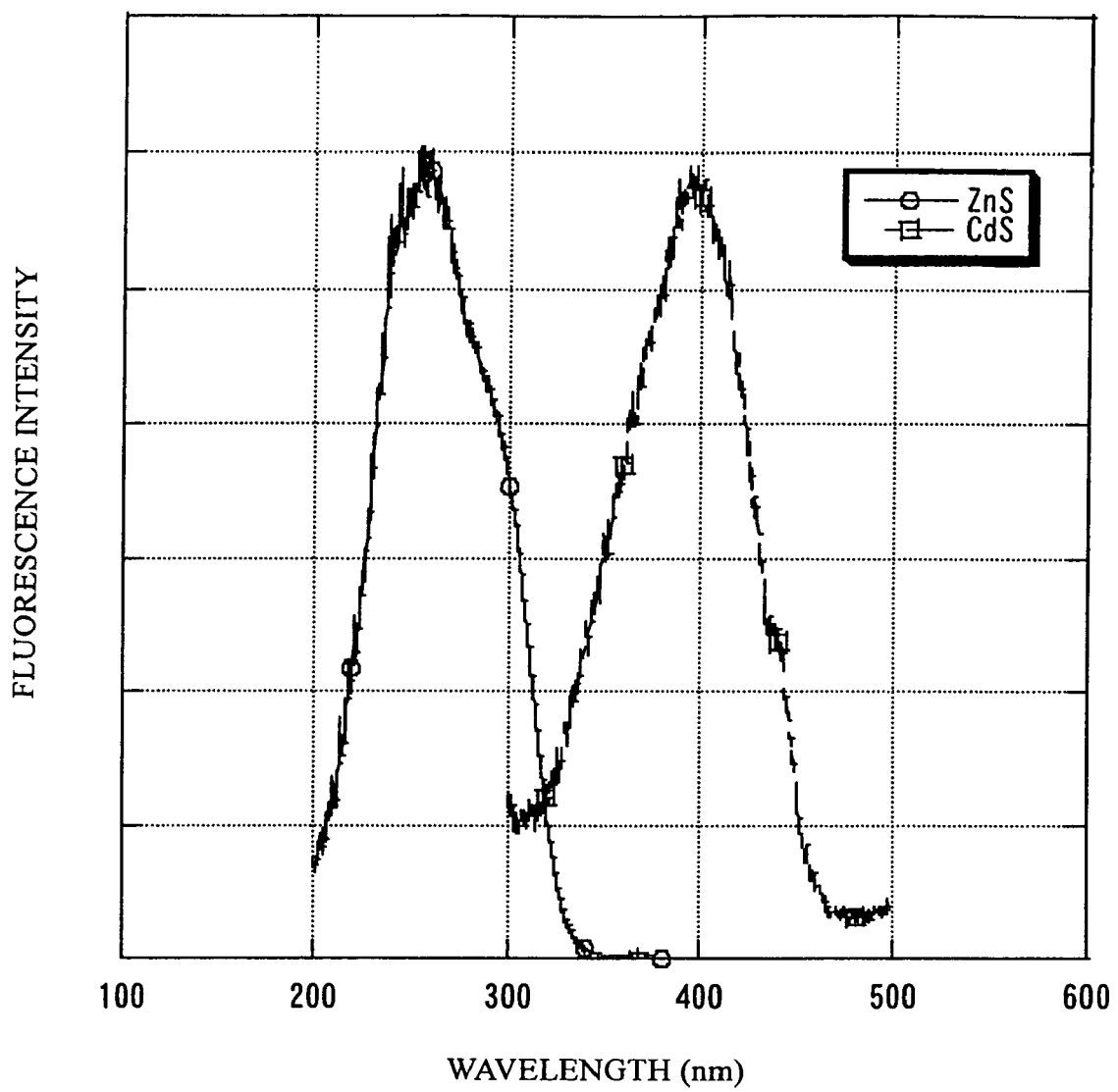
FIG. 5 shows the excitation spectra of semiconductor nanoparticles.

As shown in FIG. 1, CdS and ZnS nanoparticles exhibit different adsorption spectra from each other. In addition, FIG. 5 shows fluorescence intensities at excitation wavelengths. CdS and ZnS nanoparticles also have different excitation spectra from each other. Further, as shown in FIG. 3, they have different fluorescence spectra from each other.

When ZnS nanoparticles and CdS nanoparticles were excited at wavelengths of 250 nm and 350 nm, respectively, they exhibited fluorescence having a strong peak at wavelengths near 425 nm and 525 nm, respectively. Therefore, commonly conducted multicolor analysis and observation can be conducted with defect fluorescence of semiconductor nanoparticles by using these two fluorescent reagents simultaneously. Further, as semiconductor nanoparticles are excited at wavelengths close to 320 nm based on the excitation spectrum, semiconductor nanoparticles can thus be excited with a light source of single wavelength.

Method of Exhibiting Only Defect Fluorescence

Figure 6:
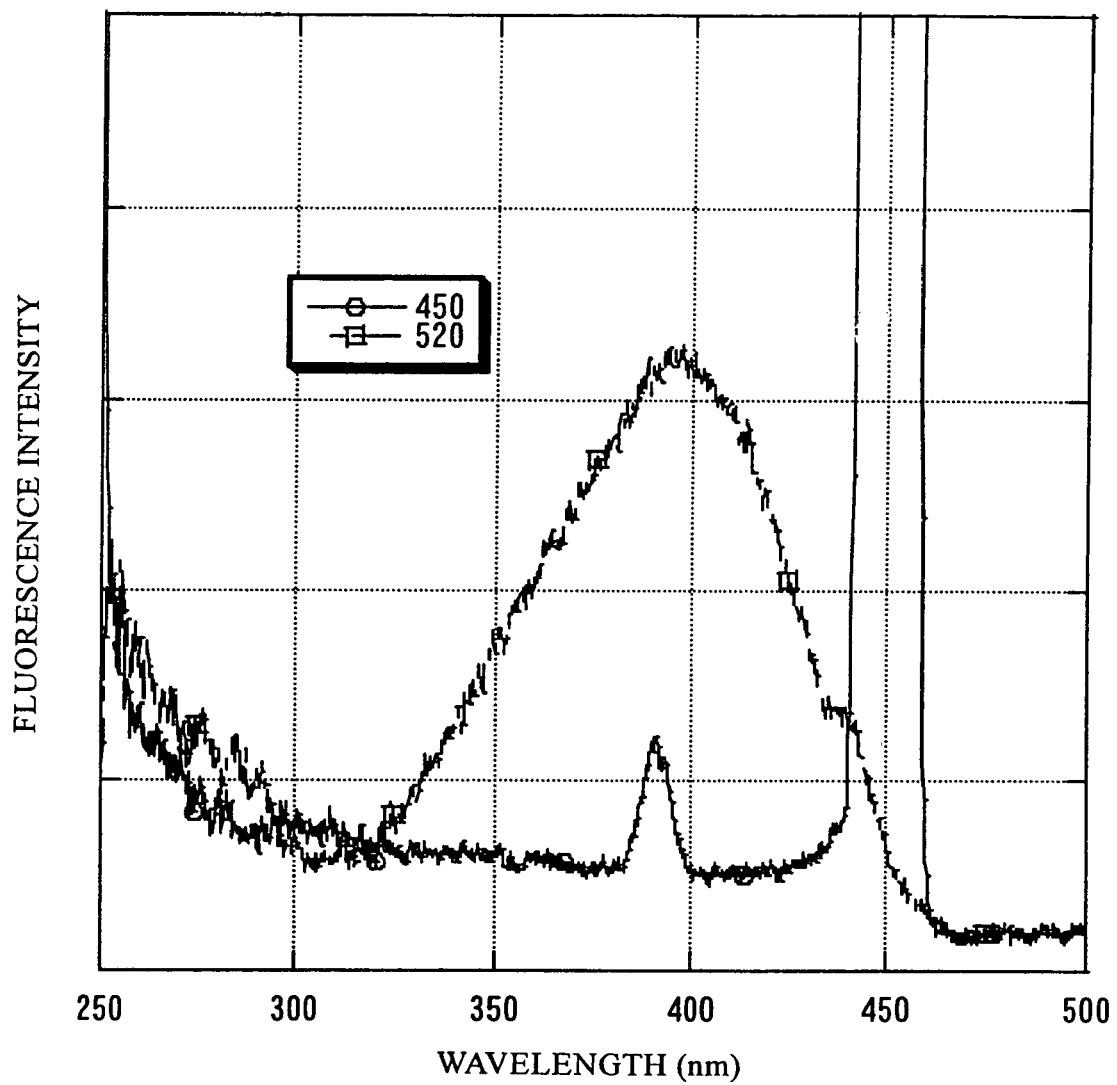
FIG. 6 shows the comparison of excitation wavelength characteristics between band gap fluorescence and defect fluorescence.

The excitation spectra of band gap fluorescence and defect fluorescence exhibit different waveforms from each other. As shown in FIG. 6, in the case of CdS semiconductor nanoparticles, the band gap fluorescence exhibited a peak at a wavelength of 450 nm, and the defect fluorescence exhibited a peak at a wavelength of 520 nm. The excitation spectra of band gap fluorescence and defect fluorescence at 450 nm and 520 nm wavelengths, respectively, both had peaks at wavelengths close to 390 nm, but the defect fluorescence spectrum had a broader full width at half maximum than the excitation spectrum of the band gap fluorescence wavelength. Hence, by exciting semiconductor nanoparticles at wavelengths deviated from a peak wavelength of fluorescence generated from the band gap or at wavelengths at which the defect fluorescence exhibits an excitation spectrum peak, it is possible to remarkably exhibit only defect fluorescence.

Analytical Method

Figure 7:
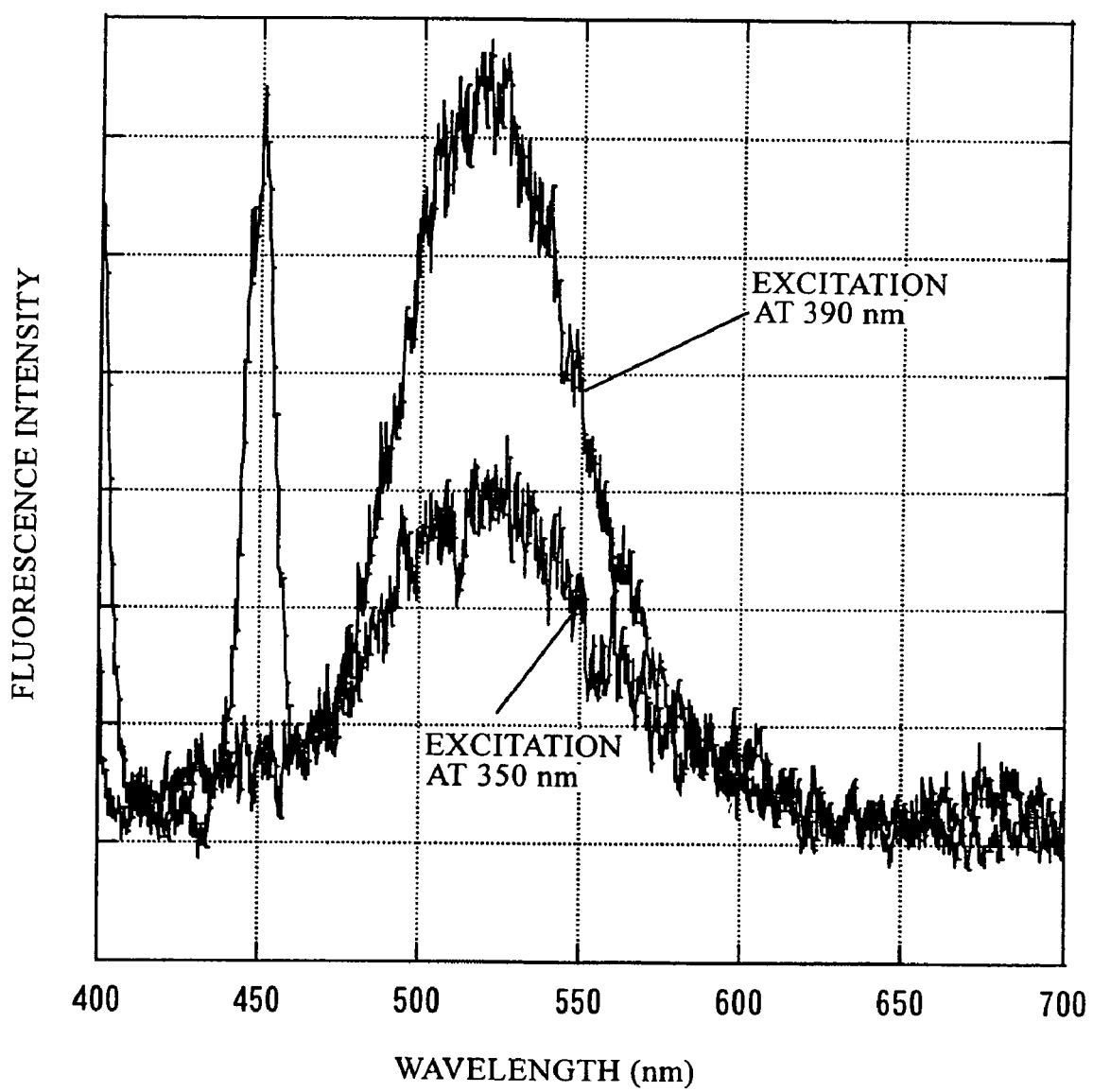
FIG. 7 shows the variations of the fluorescence characteristics by excitation wavelength.

FIG. 7 shows that the fluorescence spectra of semiconductor nanoparticles were different when the wavelength of excitation light was changed. Using these two different spectra, it is possible to perform error correction by computing the difference. Namely, the respective baselines of the spectra at 390 nm and 350 nm in FIG. 7 can be corrected based on the strength comparison between the respective excitation lights for standardization.

In the above example, the excitation was carried out with light, but the same effect can be obtained when electrically excited.

EFFECTS OF THE INVENTION

The present invention uses defect fluorescence inherent to semiconductor nanoparticles, and thus does not require any means such as an optical etching method or multi-layering to inhibit defect fluorescence. This allows manufacturers to employ an industrially suitable method for manufacturing semiconductor nanoparticles, and allows fluorescent reagents to be provided at a low price. Further, since defect fluorescence is fundamentally stronger than fluorescence generated from a band gap of semiconductor nanoparticles, various measurements or observations using semiconductor nanoparticles can be carried out easily and the measurement accuracy can be enhanced.

What is claimed is:

1. A fluorescence measurement method comprising:
   forming semiconductor nanoparticles from a material that determines a defect fluorescence of the semiconductor nanoparticles irrespective of a grain-size of the semiconductor nanoparticles;
   providing a fluorescent reagent comprising the semiconductor nanoparticles;
   binding sample biopolymers to probe biopolymers which have been immobilized on a substrate;
   electrostatically binding the semiconductor nanoparticles to sample biopolymers bound to the probe biopolymers;
   removing unbound probes from the sample polymers bound to the probe biopolymers and/or unbound semiconductor nanoparticles; and
   measuring said defect fluorescence of the semiconductor nanoparticles, which is exhibited due to the presence of a defect level mainly on a surface site of the semiconductor nanoparticles, thereby detecting an amount of the sample biopolymers bound to the probe biopolymers.

2. The fluorescence measurement method according to claim 1, wherein the sample biopolymers are bound to the probe biopolymers via hybridization.

3. The fluorescence measurement method according to claim 1, wherein the semiconductor nanoparticle is manufactured by a size-selective optical etching method.

4. The fluorescence measurement method according to claim 1, wherein the method is used for vital observation.

5. The fluorescence measurement method according to claim 4, wherein the vital observation uses each of the semiconductor nanoparticles as a stain for a living tissue in cell technologies.

6. The fluorescence measurement method according to claim 1, wherein surfaces of the semiconductor nanoparticles are modified with a functional group.

7. The fluorescence measurement method according to claim 1, further comprising measuring two or more types of defect fluorescence having different wavelengths by using two or more types of semiconductor nanoparticles to obtain two or more types of information.

8. The fluorescence measurement method according to claim 1, further comprising measuring defect fluorescence having different spectra of the semiconductor nanoparticles by changing a wavelength of excitation light to obtain a difference between the different spectra, and correcting a measurement error based on the difference.

9. The fluorescence measurement method of claim 1, wherein the sample biopolymers are not prepared by modification to incorporate active or functional groups complementary to a conjugation of the semiconductor nanoparticle.

10. The fluorescence measurement method of claim 9, wherein electrostatically binding the semiconductor nanoparticles to sample biopolymers comprises electrostatically binding the nanoparticles to a sample biopolymer, wherein the sample biopolymer has not been modified to have active or functional groups.

11. A method for detecting a sample biopolymer which comprises:
    a step of binding the sample biopolymer to a probe biopolymer which has been immobilized on a substrate;
    a step of electrostatically binding a positively or negatively charged semiconductor nanoparticle to a negative or positive charge of the sample biopolymer;
    removing unbound probes from the sample biopolymer bound to the probe biopolymer and/or unbound semiconductor nanoparticles;
    a step of exciting the semiconductor nanoparticle at wavelengths deviated from a peak wavelength of fluorescence generated from a band gap of the semiconductor nanoparticle; and
    a step of measuring defect fluorescence of the semiconductor nanoparticle to detect the presence or absence of and amount of binding of the sample biopolymer to the probe biopolymer.

12. The sample biopolymer detecting method according to claim 11, wherein the biopolymer detection uses a DNA chip or bead using hybridization.

13. The sample biopolymer detecting method according to claim 11, wherein the biopolymer is a DNA.

14. The sample biopolymer detecting method according to claim 11, wherein the biopolymer is a protein.

* * * * *